(12) United States Patent
Kompella et al.

(10) Patent No.: US 9,290,562 B2
(45) Date of Patent: Mar. 22, 2016

(54) TRANSFERRIN-TUMSTATIN FUSION PROTEIN AND METHODS FOR PRODUCING AND USING THE SAME

(75) Inventors: Uday B. Kompella, Englewood, CO (US); Robert I. Scheinman, Conifer, CO (US); Puneet Tyagi, Denver, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 14/239,176

(22) PCT Filed: Aug. 15, 2012

(86) PCT No.: PCT/US2012/051013
§ 371 (c)(1),
(2), (4) Date: Feb. 17, 2014

(87) PCT Pub. No.: WO2013/025846
PCT Pub. Date: Feb. 21, 2013

(65) Prior Publication Data
US 2014/0179612 A1    Jun. 26, 2014

Related U.S. Application Data

(60) Provisional application No. 61/524,508, filed on Aug. 17, 2011.

(51) Int. Cl.
| | | |
|---|---|---|
| *C07K 14/79* | (2006.01) | |
| *C07K 14/78* | (2006.01) | |
| *A61K 38/00* | (2006.01) | |

(52) U.S. Cl.
CPC ............. *C07K 14/79* (2013.01); *C07K 14/78* (2013.01); *A61K 38/00* (2013.01); *C07K 2319/00* (2013.01); *C07K 2319/21* (2013.01); *C07K 2319/60* (2013.01)

(58) Field of Classification Search
CPC .... C07K 14/79; C07K 14/78; C07K 2319/00; C07K 2319/21; C07K 2319/60; A61K 38/00; A61K 38/40
See application file for complete search history.

(56) References Cited

U.S. PATENT DOCUMENTS

| | | | |
|---|---|---|---|
| 7,943,733 B2 | 5/2011 | Shen et al. | |
| 2004/0023334 A1 | 2/2004 | Prior | |
| 2005/0186664 A1 | 8/2005 | Rosen et al. | |
| 2005/0192242 A1 | 9/2005 | Neal et al. | |
| 2006/0172941 A1* | 8/2006 | Rastelli et al. | 514/12 |
| 2008/0207502 A1 | 8/2008 | Rastelli et al. | |
| 2009/0170163 A1* | 7/2009 | Shen et al. | 435/69.4 |
| 2012/0244577 A1 | 9/2012 | Dixit et al. | |
| 2012/0283192 A1 | 11/2012 | Boustany et al. | |
| 2013/0143949 A1 | 6/2013 | Shen et al. | |

FOREIGN PATENT DOCUMENTS

| | | | |
|---|---|---|---|
| WO | 95/02421 | 1/1995 | |
| WO | WO 9965940 A1 * | 12/1999 | ............ C07K 14/47 |
| WO | 01/46254 | 6/2001 | |
| WO | 2006/049983 | 5/2006 | |

OTHER PUBLICATIONS

Yun Bai, Improving the Oral Efficacy of Recombinant Granulocyte Colony-Stimulating Factor and Transferrin Fusion Protein by Spacer Optimization, Pharmaceutical Research, vol. 23, No. 9, Sep. 2006.*
Yi-Qin Luo et al., "Construction, Expression, and Characterization of a New Targeted Bifunctional Fusion Protein: Tumstatin45-132-TNF," Life, Nov. 2006, vol. 58(11), pp. 647-653.
Chowers Itay et al., "The iron carrier transferrin is upregulated in retinas from patients with age-related macular degeneration," Investigative opthalmology & visual science—iovs, May 1, 2006, pp. 2135-2140, vol. 47 No. 5.
Akulapalli Sudhakar et al., "Human tumstatin and human endostatin exhibit distinct antiangiogenic activities mediated by av85 and a581 integrins," Proceedings of the national academy of sciences, Apr. 15, 2003, pp. 4766-4771, vol. 100 No. 8.
Krysten M. Farjo et al., "The potential of nanomedicine therapies to treat neovascular disease in the retina," J angiogenes res. Oct. 2010, pp. 1-14, vol. 2.

* cited by examiner

*Primary Examiner* — James H Alstrum Acevedo
*Assistant Examiner* — Erinne Dabkowski
(74) *Attorney, Agent, or Firm* — Don D. Cha; Hamilton DeSanctis & Cha, LLP.

(57) ABSTRACT

The present invention provides recombinant proteins comprising transferrin that is linked to tumstatin or other antiangiogenic protein and methods for producing and using the same. The present invention also provides an expression system, a plasmid, and a cell that is capable of expressing such recombinant proteins and methods for producing and using the same.

14 Claims, 2 Drawing Sheets

SEQUENCE LISTING

<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: Fragment of Transferrin

<400> SEQUENCE: 1

Met Arg Leu Ala Val Gly Ala Leu Leu
1               5

<210> SEQ ID NO 2
<211> LENGTH: 11
<212> TYPE: PRT
<213> ORGANISM: Artificial Sequence
<220> FEATURE:
<223> OTHER INFORMATION: Fragment of Transferrin

<400> SEQUENCE: 2

Met Arg Leu Ala Val Gly Ala Leu Leu Val Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Fragment of Transferrin

<400> SEQUENCE: 3

Leu Leu Val Cys Ala Val Leu Gly Leu Cys Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Fragment of Transferrin

<400> SEQUENCE: 4

Gly Ala Leu Leu Val Cys Ala Val Leu Gly Leu Cys Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Fragment of Transferrin

<400> SEQUENCE: 5

Leu Leu Val Cys Ala Val Leu Gly Leu Cys Leu Ala Val
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Fragment of Transferrin

<400> SEQUENCE: 6

Gly Ala Leu Leu Val Cys Ala Val Leu Gly Leu Cys Leu Ala Val
1               5                   10                  15

<210> SEQ ID NO 7
<211> LENGTH: 24
<212> TYPE: PRT
<213> ORGANISM: Artificial Sequence
<220> FEATURE:
<223> OTHER INFORMATION: Fragment of Transferrin

<400> SEQUENCE: 7

Met Arg Leu Ala Val Gly Ala Leu Leu Val Cys Leu Val Cys Ala
1               5                   10                  15

Val Leu Gly Leu Cys Leu Ala Val
            20

<210> SEQ ID NO 8
<211> LENGTH: 16
<212> TYPE: PRT
<213> ORGANISM: Artificial Sequence
<220> FEATURE:
<223> OTHER INFORMATION: Fragment of Transferrin

<400> SEQUENCE: 8

Gly Phe Gln Asn Leu Asn Ile Gly Cys Leu Lys Glu Lys Ala Val Ala
1               5                   10                  15

<210> SEQ ID NO 9
<211> LENGTH: 27
<212> TYPE: PRT
<213> ORGANISM: Artificial Sequence
<220> FEATURE:
<223> OTHER INFORMATION: Portion of Transferrin

<400> SEQUENCE: 9

Leu Leu Cys Thr Arg Asp Glu Ile Leu Thr Glu Lys Leu Glu Trp Cys
1               5                   10                  15

Ile Asn Glu Ala Asp Leu Val Pro Glu Asn Tyr
            20                  25

<210> SEQ ID NO 10
<211> LENGTH: 9
<212> TYPE: PRT
<213> ORGANISM: Artificial Sequence
<220> FEATURE:
<223> OTHER INFORMATION: Portion of Transferrin

<400> SEQUENCE: 10

Pro Arg Lys Pro Leu Glu Lys Ala Val
1               5

<210> SEQ ID NO 11
<211> LENGTH: 5
<212> TYPE: PRT
<213> ORGANISM: Artificial Sequence
<220> FEATURE:
<223> OTHER INFORMATION: Portion of Tumstatin

<400> SEQUENCE: 11

Tyr Ser Asn Ser Gly
1               5

<210> SEQ ID NO 12
<211> LENGTH: 25
<212> TYPE: PRT
<213> ORGANISM: Artificial Sequence
<220> FEATURE:
<223> OTHER INFORMATION: Artificial Peptide

```
<400> SEQUENCE: 12

Thr Met Pro Phe Leu Phe Cys Asn Val Asn His Val Cys Asn Phe Ala
1               5                   10                  15

Ser Arg Asn His Tyr Ser Tyr Trp Leu
            20                  25

<210> SEQ ID NO 13
<211> LENGTH: 25
<212> TYPE: PRT
<213> ORGANISM: Artificial Sequence
<220> FEATURE:
<223> OTHER INFORMATION: Artificial Peptide

<400> SEQUENCE: 13

Thr Met Pro Phe Leu Phe Cys Asn Val Asn Asp Val Cys Asn Phe Arg
1               5                   10                  15

Ser Arg Asn Asp Tyr Ser Tyr Trp Leu
            20                  25

<210> SEQ ID NO 14
<211> LENGTH: 25
<212> TYPE: PRT
<213> ORGANISM: Artificial Sequence
<220> FEATURE:
<223> OTHER INFORMATION: Artificial Peptide

<400> SEQUENCE: 14

Thr Met Pro Phe Leu Phe Cys Asn Val Asn Asp Val Cys Asn Phe Ala
1               5                   10                  15

Ser Arg Asn Asp Tyr Ser Tyr Trp Arg
            20                  25

<210> SEQ ID NO 15
<211> LENGTH: 19
<212> TYPE: PRT
<213> ORGANISM: Artificial Sequence
<220> FEATURE:
<223> OTHER INFORMATION: Artificial Peptide

<400> SEQUENCE: 15

Cys Asn Tyr Tyr Ser Asn Ser Tyr Ser Phe Trp Leu Arg Ser Leu Asn
1               5                   10                  15

Pro Glu Arg

<210> SEQ ID NO 16
<211> LENGTH: 19
<212> TYPE: PRT
<213> ORGANISM: Artificial Sequence
<220> FEATURE:
<223> OTHER INFORMATION: Artificial Peptide

<400> SEQUENCE: 16

Cys Asn Tyr Tyr Ser Asn Ser Tyr Ser Phe Trp Leu Ala Ser Arg Asn
1               5                   10                  15

Pro Glu Arg

<210> SEQ ID NO 17
<211> LENGTH: 33
<212> TYPE: DNA
<213> ORGANISM: Artificial Sequence
<220> FEATURE:
<223> OTHER INFORMATION: Artificial Oligonucleotide
```

```
<400> SEQUENCE: 17
cgatggatcc gcaacctgga caacgagagg ctt                               33

<210> SEQ ID NO 18
<211> LENGTH: 33
<212> TYPE: DNA
<213> ORGANISM: Artificial Sequence
<220> FEATURE:
<223> OTHER INFORMATION: Artificial Oligonucleotide

<400> SEQUENCE: 18
cgatctcgag agtgtctttt cttcatgcac acc                               33

<210> SEQ ID NO 19
<211> LENGTH: 32
<212> TYPE: DNA
<213> ORGANISM: Artificial Sequence
<220> FEATURE:
<223> OTHER INFORMATION: Artificial Oligonucleotide

<400> SEQUENCE: 19
atcgataagc tttgtgagca agggcgagga gc                                32

<210> SEQ ID NO 20
<211> LENGTH: 32
<212> TYPE: DNA
<213> ORGANISM: Artificial Sequence
<220> FEATURE:
<223> OTHER INFORMATION: Artificial Oligonucleotide

<400> SEQUENCE: 20
atcgatggat cccttgtaca gctcgtccat gc                                32

<210> SEQ ID NO 21
<211> LENGTH: 32
<212> TYPE: DNA
<213> ORGANISM: Artificial Sequence
<220> FEATURE:
<223> OTHER INFORMATION: Artificial Oligonucleotide

<400> SEQUENCE: 21
agtcgctagc atgaggctcg ccgtgggagc cc                                32

<210> SEQ ID NO 22
<211> LENGTH: 41
<212> TYPE: DNA
<213> ORGANISM: Artificial Sequence
<220> FEATURE:
<223> OTHER INFORMATION: Artificial Oligonucleotide

<400> SEQUENCE: 22
agtcgcggcc ggctgggcca ggtctacgga aagtgcaggc t                      41
```

TRANSFERRIN-TUMSTATIN FUSION PROTEIN AND METHODS FOR PRODUCING AND USING THE SAME

CROSS-REFERENCE TO RELATED APPLICATIONS

This application is U.S. National Stage Application of PCT Patent Application No. PCT/US2012/051013, filed on Aug. 15, 2012, which claims the priority benefit of U.S. Provisional Application No. 61/524,508, filed Aug. 17, 2011, all of which are incorporated herein by reference in their entirety.

FIELD OF THE INVENTION

The present invention relates to recombinant proteins comprising transferrin that is linked to tumstatin or other antiangiogenic protein and methods for producing and using the same. The present invention also relates to expression system that is capable of expressing such recombinant proteins and methods for producing and using the same.

BACKGROUND OF THE INVENTION

Choroidal neovascularization (CNV) refers to the uncontrolled growth of choroidal vasculature which can lead to severe vision loss in diseases such as pseudoxanthoma elasticum, angioid streaks, histoplasmosis, punctuate inner choroidopathy and wet age related macular degeneration (AMD). Wet AMD occurs when the deposition of drusen (complement components, lipids, and apolipoproteins) causes confined ischemic regions resulting in hypoxia. It is believed that hypoxia leads to an increase in the secretion of vascular endothelial growth factor (VEGF), which activates choroidal endothelial cells to secrete matrix metalloproteinases (MMP). Metalloproteinases degrade the extracellular matrix, thereby allowing for the proliferation of endothelial cells and their migration towards the retina. The effect of MMP eventually results in the development of new blood vessels, or CNV, which can cause retinal detachment and hemorrhage and the formation of sub retinal lesions due to blood and lipid leakage. Once manifested, CNV is a major cause of vision loss in the elderly population of industrialized nations.

Treatment of CNV is currently limited to a fraction of the patient population and focuses on restraining the detrimental role of VEGF in vascular hyperpermeability and new blood vessel formation. However, VEGF also plays a constructive key role in physiological activities such as wound healing, photoreceptor survival, and maintaining the choroid capillary bed. Currently, Ranibizumab (Lucentis™), Aflibercept (Eylea™) and pegaptanib (Macugen™) are the only two therapeutic agents that have been approved to date to treat CNV. These agents inhibit VEGF. It has been shown that ranibizumab is generally more effective than pegaptanib in treating CNV. Ranibizumab binds to all isoforms of VEGF-A and inhibits VEGF activity including vascular permeability and growth. Other than the two mentioned therapeutic agent, bevacizumab (Avastin™), the parent full length antibody of ranibizumab, is also being explored as an off label treatment for CNV.

Despite the success of these therapies in treating CNV there are inherent drawbacks in these therapies, including lack of apoptosis in activated endothelial cells, and potential impairment of VEGF related physiological activities such as wound healing. In addition, use of ranibizumab leads to systemic risks including increased rate of thromboembolic events after intravitreal administration in humans. Intravitreal bevacizumab has also been associated with ischemic attack, blood pressure elevation, cerebrovascular accidents, and death. Further, in a clinical trial with patients suffering from CNV, the response rate to ranibizumab was only ~40% in patients with CNV and the gain in number of letters was only 7.2.

Therefore, there is a need for new and/or more effective therapeutic approach for treating CNV that has reduced side effects and/or better therapeutic efficacy.

SUMMARY OF THE INVENTION

Some aspects of the invention provide a recombinant protein comprising transferrin that is linked to tumstatin or other similar antiangiogenic protein. In some embodiments, transferrin and tumstatin are directly linked to one another. Yet in other embodiments, transferrin and tumstatin are covalently linked to one another through a linker. Suitable linkers are well known to one skilled in the art.

Other aspects of the invention provide a plasmid comprising a nucleic acid sequence encoding a recombinant protein comprising transferrin that is linked to tumstatin. Typically, the nucleic acid sequence encoding the recombinant protein is operatively linked to an expression control sequence.

Still other aspects of the invention provide a recombinant nucleic acid molecule comprising a nucleic acid sequence encoding a recombinant protein comprising transferrin that is linked to tumstatin. In some embodiments, the nucleic acid sequence is operatively linked to an expression control sequence.

Yet other aspects of the invention provide a recombinant host cell that is transfected with and expresses the recombinant nucleic acid molecule comprising a nucleic acid sequence encoding a recombinant protein comprising transferrin that is linked to tumstatin.

Other aspects of the invention provide a method for producing a recombinant protein comprising transferrin that is linked to tumstatin, said method comprising:
  transfecting a recombinant host cell with a recombinant nucleic acid molecule comprising a nucleic acid sequence encoding a recombinant protein comprising transferrin that is linked to tumstatin;
  culturing the transfected host cell under conditions sufficient to produce the recombinant protein comprising transferrin that is linked to tumstatin; and
  recovering the recombinant protein as a substantially purified recombinant protein.

In some embodiments, the recombinant protein comprises transferrin that is directly linked to tumstatin.

Still other aspects of the invention provide a method for treating a clinical condition associated with choroidal neovascularization (CNV) in a subject, said method comprising administering to the subject in need of such a treatment a therapeutically effective amount of a recombinant protein comprising transferrin that is linked to tumstatin.

In some embodiments, the clinical condition associated with CNV comprises pseudoxanthoma elasticum, angioid streaks, histoplasmosis, punctuate inner choroidopathy, or wet age related macular degeneration (AMD).

Compositions of the invention can also be used to treat other diseases such as, but not limited to, cancer; cancer associated neovascularization; corneal angiogenesis; proliferative diabetic retinopathy; neovascular glaucoma; other neovascular and vascular proliferative disorders of the eye; as well as other neovascular and vascular proliferative disorders elsewhere in the body.

Compositions of the invention can be administered using any of the methods known to one skilled in the art including, but not limited to, intravitreal, intravenous, suprachoroidal, topical, periocular, subcutaneous, intramuscular, subretinal, retrobulbar, intrascleral, etc.

DETAILED DESCRIPTION OF THE INVENTION

Some aspects of the invention provide a recombinant protein comprising transferrin that is linked (i.e., attached) to tumstatin. Transferrin can be linked directly or indirectly (e.g., via a linker) to tumstatin. Other aspects of the invention provide a recombinant nucleic acid molecule comprising a nucleic acid sequence encoding a recombinant protein comprising transferrin that is linked to tumstatin. Still other aspects of the invention provide recombinant host cells that are transfected with and express the recombinant nucleic acid molecule comprising a nucleic acid sequence encoding a recombinant protein comprising transferrin that is linked to tumstatin. Yet other aspects of the invention provide methods for producing and using a recombinant protein comprising transferrin that is linked to tumstatin.

Tumstatin has been shown to be therapeutically effective in treating CNV. Without being bound by any theory, it is believed that tumstatin has the ability to regress angiogenesis by causing apoptosis, an attribute lacking in current CNV therapies.

Tumstatin is an endogenous angiogenesis inhibitor which was initially obtained from the C terminus non-collagenous domain (NC1) of Collagen IV present in the basement membrane. It is believed that tumstatin plays a role in inhibiting blood vessel formation by binding to αVβ3 integrins, hindering the proliferation of endothelial cells and also by inducing endothelial cell apoptosis. In the absence of any pathological condition, a balance is maintained between angiogenic (such as VEGF) and antiangiogenic molecules (such as tumstatin). During, hypoxia and ischemia, the balance between angiogenic and antiangiogenic molecules is believed to be perturbed, thereby causing neovascularization. Angiogenesis inhibitors like tumstatin are a part of the body's inherent mechanism to fight neovascularization.

Tumstatin has many advantages over ranibizumab and bevacizumab and is believed to be therapeutically better than these antibodies. To date, the tumstatin receptor, αVβ3 integrin, is found only on activated endothelial cells and not on normal vessels. Accordingly, it is believed that tumstatin provides a path to target activated endothelial cells, without affecting physiological processes such as wound healing. Tumstatin promotes apoptosis in endothelial cells, and it is believed that apoptosis caused by tumstatin can result in regression of proliferating blood vessels, and thus is advantageous in restoring normal vision. Accordingly, tumstatin can effectively treat neovascularization and prevent vision loss without any significant anti-VEGF therapy related side effects.

Surprisingly and unexpectedly, the present inventors have discovered that tumstatin's therapeutic efficacy in CNV can be significantly increased by linking tumstatin to another protein. In one particular embodiment, tumstatin was linked to transferrin in order to achieve polarized secretion of the fusion protein from the retinal pigment epithelium (RPE cells). When exposed to the RPE monolayer, the fusion protein was secreted preferably towards the basolateral side, when compared to tumstatin. After transfection with transferrin-tumstatin gene, the transferrin-tumstatin protein formed was secreted more towards the basolateral direction in polarized epithelial cell monolayers, when compared to tumstatin gene product. Basolateral secretion of a recombinant transferrin-tumstatin protein delivered tumstatin in close proximity to the activated and neovascular choroid endothelial cells, thereby enhancing the therapeutic activity of tumstatin. Without being bound by any theory, it is believed that the enhanced basolateral secretion of transferrin-tumstatin is prominent in the eyes of patients suffering from AMD since iron content and transferrin receptor activity is likely elevated in the eyes of these patients. It is believed that the most accessible route for iron elimination is via choroid vasculature. This route also leads to increased secretion of transferrin (and thus the recombinant transferrin-tumstatin protein) towards the choroid.

Based on the foregoing, the present inventors investigated a novel transferrin-tumstatin fusion protein (i.e., a recombinant transferrin-tumstatin protein) as well as tumstatin for their efficacy in inhibiting migration, proliferation, and tube formation of choroid endothelial cells. These activities were compared with those of bevacizumab. Furthermore, the present inventors have determined the ability of the recombinant protein of the present invention to be secreted in a polarized manner in a well established polarized cell model (e.g., Madin-Darby canine kidney, i.e., MDCK, cells).

As used herein, the term "transferrin" includes therapeutically effective fragments of transferrin. In some embodiments, the term "transferrin" refers to a peptide having at least a peptide fragment of transferrin that can bind integrins. Alternatively, the term "transferrin" typically refers to a peptide having at least 5 amino acids of the full transferrin peptide sequence. Still alternatively, the term "transferrin" refers to a peptide having at least 25%, typically at least 50%, often at least 75%, and still more often at least 90% of the full transferrin peptide sequence, as long as that fragment is capable of selectively binding to integrins. Accordingly, any therapeutically effective fragment of transferrin can be used for targeted uptake and secretion of the recombinant protein towards the neovascular regions (e.g., secretion towards choroid). In some embodiments, the therapeutically effective fragment of transferrin comprises a peptide fragment of transferrin that can bind, typically selectively, integrins.

Some fragments of transferrin with biological activity are known to one skilled in the art. It should be appreciated that the scope of the invention includes the full-length transferrin and tumstatin proteins as well as fragments of one or both of these proteins as long as such a recombinant protein has a desired biological activity. Whether a particular fragment of transferrin and/or tumstatin has a desired biological activity can be readily determined by one skilled in the art using the in vitro and in vivo experimentations, such as those disclosed herein. Accordingly, the scope of the invention includes any therapeutic fusion proteins (i.e., recombinant tumstatin-transferrin proteins) for treating neovascular disorders, where tumstatin and/or transferrin can be independently a whole protein or a fragment thereof. It is believed that the recombinant proteins are typically more therapeutically efficient than the parent proteins. Compositions of the invention include recombinant proteins or nucleic acid constructs capable of expressing the recombinant proteins in relevant cells.

Series I Peptides. Fragments of Transferrin

Discussed herein are some of the representative fragments of transferrin that are capable of conferring basolateral secretion and methods for identifying and producing the same.

Transferrin protein sequence as well as the sequences of various secretory proteins were analyzed and fragments of transferrin suitable for the generation of new fusion proteins capable of basolateral secretion/transport were identified. Analysis of the peptide sequence of various basolaterally secreted proteins such as interleukin 6 (Holtkamp et al., *Clin Exp Immunol.*, 1998, 112(1), 34-43), interleukin 8 (id.), and vascular endothelial growth factor A (VEGF-A) (Sonoda et al., *AGING*, 2010, 2(1), 28-42) led to identification of a surprising similarity in the N terminal amino acids of such proteins. It is believed that proteins including interleukin 6, interleukin 8, and vascular endothelial growth factor A (VEGF-A) are secreted on the basolateral side and have an abundance of leucine amino acid. Furthermore, dileucines (i.e., "LL") are also present near the N terminal of these proteins. Based on these understandings, the present inventors have identified the following representative peptides in transferrin that can be responsible for the basolateral secretion of transferrin-tumstatin: MRLAVGALL (SEQ ID NO:1); MRLAVGALLVC (SEQ ID NO:2); LLVCAVLGLCL (SEQ ID NO:3); GALLVCAVLGLCL (SEQ ID NO:4); LLVCAVLGLCLAV (SEQ ID NO:5); GALLVCAVLGLCLAV (SEQ ID NO:6); and MRLAVGALLVCLLVCAVLGLCLAV (SEQ ID NO:7). Accordingly, in some embodiments any peptide or recombinant peptide comprising these peptides are suitable for effecting basolateral secretion of transferrin-tumstatin. These peptides (i.e., fragments of transferrin disclosed herein), when fused with tumstatin or any other suitable therapeutic protein, result in basolateral secretion of the therapeutic protein (e.g., across retinal pigment epithelium towards the choroid).

Series II Peptides. Peptides of Transferrin Capable of Binding Integrins:

Surprisingly and unexpectedly, the present inventors have also discovered that transferrin protein can interact with αVβ3 integrin receptor, in addition to its expected interaction with transferrin receptor. The recombinant transferrin-tumstatin protein of the invention is believed to interact with the αVβ3 integrin receptor, which is the receptor for tumstatin, and also with the transferrin receptor, due to the presence of transferrin. Using in silico docking of transferrin-tumstatin to αVβ3 integrin receptor, the present inventors have identified the amino acids within transferrin protein that interact with the integrin receptor. The following amino acids are some of the representative peptides that are believed to interact with the integrin receptor based on in silico docking:

Q(127), N(129), L(131), N(148), I(151), G(152), C(156), L(158), K(163), E(166), K(167), A(168); and C(246), T(250), R(251), D(259), E(337), 1(342), L(345), T(349), E(357), K(359), L(366), E(370), W(377), C(396), 4400), N(402), E(404), A(405), D(406), L(423), V(424), P(425), E(429).

Based on these interacting amino acids, the following peptides of transferrin were designed as those capable of interacting with integrin receptors: GFQNLNIGCLKEKAVA (SEQ ID NO:8); LLCTRDEILTEKLEWCINEADLVPENY (SEQ ID NO:9); Transferrin$_{127-168}$; Transferrin$_{125-170}$; Transferrin$_{246-259}$; Transferrin$_{244-261}$; Transferrin$_{337-429}$; and Transferrin$_{335-431}$. As used herein, the term Transferrin$_{x-y}$ refers to amino acid sequences of transferrin beginning on amino acid "x" and ending at amino acid "y".

Series III Peptides. Fragments of Transferrin Capable of Binding to Transferrin Receptor:

Disclosed below are some of the representative fragments of transferrin that are found to be capable of binding to transferrin receptor.

It is believed that the following amino acids in transferrin interact with transferrin receptor. Transferrin$_{161-169}$; H(368), R(371), L(372), D(375), E(376), S(378), V(379); PRKPLEKAV (SEQ ID NO:10); Transferrin$_{159-171}$; Transferrin$_{368-379}$; and Transferrin$_{366-381}$. Accordingly, these fragments of transferrin can also be used in methods of the present invention.

Series IV Peptides. Fragments of Tumstatin with Anti-Angiogenic and/or Anti-Tumor Activity The term "tumstatin" includes therapeutically effective fragments of tumstatin. In particular, the term "tumstatin" includes portions or fragments of tumstatin peptide that can increase the delivery of transferrin relative to using transferrin without any additional tumstatin peptide. Accordingly, in some embodiments, the term "tumstatin" refers to a peptide having at least a peptide fragment of tumstatin that can increase the therapeutic effectiveness of transferrin relative to transferrin without such a peptide. Alternatively, the term "tumstatin" refers to a peptide having at least 25%, typically at least 50%, often at least 75%, and more often at least 90% of the full tumstatin peptide sequence. Some fragments of tumstatin with biological activity (e.g., anti-angiogenic activity) are known to one skilled in the art. It should be appreciated that the scope of the invention (as well as the term "tumstatin") includes the full-length tumstatin proteins as well as fragments thereof.

Tumstatin is an angiogenesis inhibitor that binds to αVβ3 integrin receptor and suppresses tumor growth. Previous deletion mutagenesis studies (see, for example, Eikesdal et al., *PNAS*, 2008, 105(39), 15040-15045; and Thevenard et al., *Int. J. Cancer*, 2010, 126, 1055-1066) have identified the following amino acid fragments of tumstatin with antiangiogenic activity: Tumstatin$_{74-98}$; Tumstatin$_{185-203}$; and YSNSG (SEQ ID NO:11).

The present inventors have also designed novel peptides based on the above peptide sequence by in silico protein modeling. In one particular embodiment, D (aspartic acid) was replaced with H (histidine) at two points as shown below:

```
                                        (SEQ ID NO: 12)
         TMPFLFCNVNHVCNFASRNHYSYWL
```

It is believed that replacing H with D results in a net favorable electrostatic interaction between the positive charge of H and the other protein charges. In some other embodiments, the hydrophobic residues alanine (A) and leucine (L) were replaced with arginine (R), a hydrophilic amino acid. Some of these modified peptides include:

```
                                        (SEQ ID NO: 13)
         TMPFLFCNVNDVCNFRSRNDYSYWL;

(SEQ ID NO: 14)
         TMPFLFCNVNDVCNFASRNDYSYWR;

(SEQ ID NO: 15)
         CNYYSNSYSFWLRSLNPER;
         and
```

CNYYSNSYSFWLASRNPER. (SEQ ID NO: 16)

Arginine contains a guanidinium group, which is responsible for its polarity. It is believed that replacing hydrophobic residues with hydrophilic arginine helps in improving the stability of the protein by virtue of additional hydrogen bonds formed with the solvent. Furthermore, it is believed that arginine, whose guanidinium group is positively charged at pH 7.4, will introduce a charge on the surface and provide an avenue for additional interactions on the protein surface. Any of the above natural sequences or modified fragments can be used in creating fusion or recombinant proteins of the invention. Accordingly, it should be appreciated that the terms "transferrin" and "tumstatin" includes those modifications where one or more of the amino acid residues are replaced with a non-wild type amino acids including homolog amino acids. One skilled in the art can readily determine a suitable amino acid substitution having read the present disclosure.

As discussed above, in addition to the full-length recombinant proteins of transferrin and tumstatin, the scope of the invention includes recombinant proteins in which one or both of the full-length proteins of transferrin and/or tumstatin are replaced with any of the corresponding partial peptides disclosed above.

Accordingly, the scope of the invention includes recombinant proteins where any combination of a peptide/protein from peptides disclosed in Series I or III Peptides above or transferrin itself with the peptide in Series II or IV Peptides above or tumstatin itself (e.g., a Series I Peptide fused with any therapeutic protein or peptide such as tumstatin or a peptide of Series II or IV Peptide; and Series II Peptide fused with Series I Peptide, etc.). Additionally, a Series I Peptide can be combined with any new therapeutic macromolecule for targeted uptake/transport/secretion.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Materials and Methods

Example 1

Materials: Transwell® filters (0.4 μm pore size) were purchased from Corning Inc., NY. Bovine serum albumin was purchased from Sigma Aldrich (MO). BD Matrigel Matrix Growth Factor Reduced was purchased from BD Biosciences (CA). DNA ladder, Lipofectamine® 2000 reagent and DAPI stain was purchased from Invitrogen Corporation (CA). The restriction enzymes used were purchased from New England Biolabs (MA). The QuikChange® Site-Directed Mutagenesis Kit was purchased from Agilent Technologies (CA). Transferrin gene, choroid endothelial cells (RF/6A), and the RF/6A cell media were purchased from American Type Culture Collection, VA. QIAGEN® plasmid Giga kit was purchased from QIAGEN Inc. (CA). TALON® metal affinity resin (Catalogue #635502) was purchased from Clonetech Laboratories, Inc. (CA). BCA® Protein Assay Kit, used to estimate protein content, was purchased from Pierce Biotechnology, Inc. (IL) (Catalogue #23225). Readymade gels, 10% Ready Gel Tris-HCl® from Bio-Rad laboratories, Inc. (CA) and EZ Run® prestained protein ladder from Fisher Scientific (PA) were used during SDS PAGE gel electrophoresis. A BCA® protein assay kit was purchased from Thermo Fisher Scientific (IL).

Figure 4:
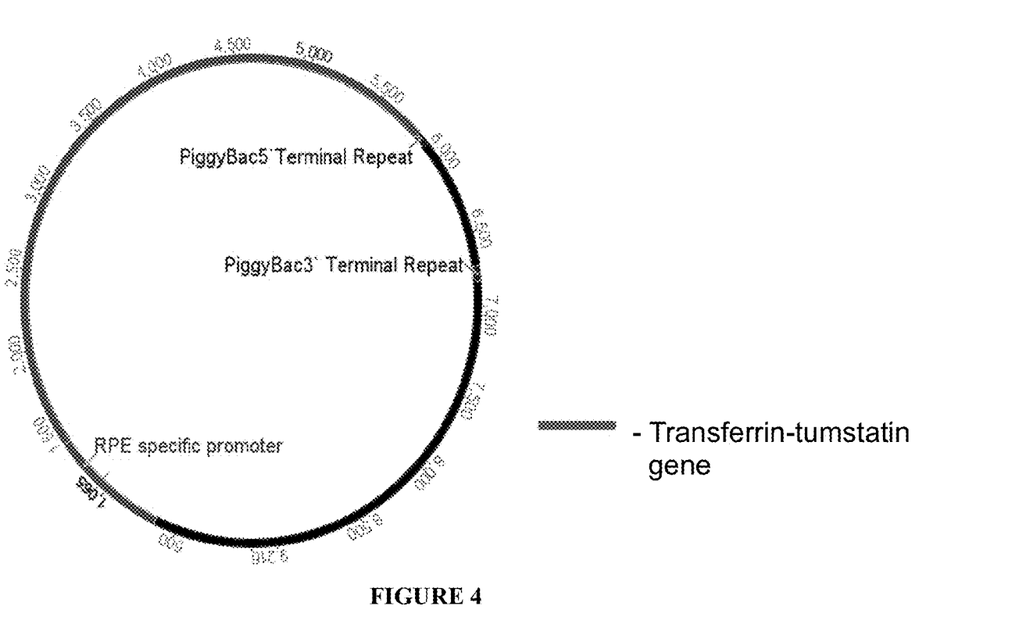
FIG. 4 is a schematic representation transferrin-tumstatin sustained gene expression construct.

Construction of Plasmids:

Four different constructs were prepared for the study, containing the following cDNAs, namely, (a) Tumstatin; (b) Tumstatin-EGFP; (c) Transferrin-tumstatin (see FIG. 4 which schematically illustrates transferrin-tumstatin sustained gene expression construct. A similar construct with transferrin is useful for long-term expression of tumstatin); and (d) Transferrin-tumstatin-EGFP. All primers were purchased from Integrated DNA Technologies Inc. (CA) for use in this experiment. Tumstatin cDNA was PCR amplified using forward primer (5'-CGATGGATCCGCAACCTGGACAAC-GAGAGGCTT-3') (SEQ ID NO:17) and reverse primer (5'-CGATCTCGAGAGTGTCTTTTCTTCATGCACACC-3') (SEQ ID NO:18) and ligated into vector PSecTag2B as a BamHI and XhoI fragment. EGFP was cloned into PSecTag2B vector as a Hind III and BamHI fragment using the pEGFP vector (Clonetech Laboratories, CA) as a template and using forward primer (5'-ATCGATAAGCTTTGTGAG-CAAGGGCGAGGAGC-3') (SEQ ID NO:19) and reverse primer (5'-ATCGATGGATCCCTTGTACAGCTCGTC-CATGC-3') (SEQ ID NO:20).

The IgK secretory sequence was swapped for transferrin by first digesting our construct with Nhe1 plus Sfi1 to remove the IgK sequence. Transferrin was amplified using the forward primer (5'-AGTCGCTAGCATGAGGCTCGCCGTGG-GAGCCC-3') (SEQ ID NO:21) and reverse primers (5'-AGTCGCGGCCGGCTGGGCCAGGTCTACG-GAAAGTGCAGGCT-3') (SEQ ID NO:22) containing and restriction sites, Nhe1 and Sfi1 sites, respectively, and cloned into the linearized vector. Transferrin was incorporated into the PsecTag2B containing Tumstatin and pEGFP. The Igk gene portion of PSecTag2B was removed during this process. The same forward and reverse primers were used to incorporate Transferrin into a PsecTag2B vector containing only Tumstatin to make transferrin-tumstatin plasmid.

All plasmids were grown using the dH5α strain of *E. Coli* bacteria and amplified using QIAGEN® plasmid Giga kit. A 1% agarose gel was prepared in TAE buffer and used to study the cDNA constructs. Pictures were taken using the GelDoc XR® imaging system (Bio-Rad laboratories, Inc. CA).

Production and Purification of Protein:

The PSecTag2B vector used to construct plasmids, as mentioned above, has a six histidine tag that can aid in purification of the protein secreted in the media. The plasmid was transfected in ARPE (human retinal pigment epithelium) cells to express the fusion proteins created. ARPE cells were grown until 80% confluency was attained. Transient transfection of the ARPE cells was performed using the Lipofectamine® 2000 reagent. TALON® metal affinity resin was used to purify the histidine tagged protein. BCA® Protein Assay Kit was used to estimate the elute's protein content. A protein estimation standard curve was made using Bovine serum Albumin (Sigma Aldrich, MO).

Confocal Microscopy of ARPE Cells:

The tumstatin-EGFP plasmid was studied in APRE cells to see the functioning of EGFP gene in the cells. ARPE cells were grown until 80% confluency was attained. Transient transfection of the ARPE cells was performed using Lipofectamine® 2000 reagent. DAPI (4',6-diamidino-2-phenylindole, dihydrochloride) staining was done for the cell nuclei. ARPE cells with no transfection with tumstatin—EGFP plasmid and only DAPI staining were used as control.

To study the internalization of transferrin-tumstatin-EGFP and tumstatin-EGFP, protein choroidal endothelial cells were exposed to transferrin-tumstatin-EGFP and tumstatin-EGFP protein for 24 hours. After 24 hours the cells were washed with cold PBS pH 7.4 followed by washing with cold acidic buffer (pH 5.0) and fixed using 4% paraformaldehyde and stained with DAPI. Cells were observed under a Nikon C1si® confocal microscope.

Polarized Secretion of Transferrin-Tumstatin-EGFP Fusion Protein:

The MDCK cell line was chosen for the fusion protein polarized secretion study as it is a polarized system that is well understood. MDCK cells have routes that deliver membrane proteins to the apical or basolateral surface.

MDCK cells were plated on Transwell filters and Trans epithelial electrical resistance (TEER) was measured using an EVOM® resistance meter (World Percision Instruments, CA). When TEER was above 300Ω, the cells were transfected with tumstatin-EGFP or transferrin-tumstatin-EGFP plasmid as described above. After 24 hours of transfection, the MDCK cells were fixed and stained using DAPI nuclei stain. The media was collected from both the basolateral and the apical side separately and fusion proteins were quantified using a BCA® protein assay kit.

Cell proliferation assay: Choroid endothelial cells (RF/6A) were used to study the effect of tumstatin protein and transferrin-tumstatin protein on the proliferation of cells under the effect of VEGF 165. An MTT assay was used to evaluate cell proliferation.

The choroid endothelial cells (RF/6A, passage#9) were plated in a 96-well plate at a seeding density of about 20,000 cells/well and allowed to adhere to the well for 24 hours. After 24 hours, cells were incubated with solutions of VEGF165 (R&D systems, MN) in a concentration of 50 ng/ml. The proliferation of RF/6A cells was induced by using 50 ng/mL of VEGF 165. Out of the 96 wells, 3 wells were kept as controls, containing only RF/6A cells and 50 ng/mL of VEGF 165. The remaining wells contained bevacizumab, tumstatin, or transferrin-tumstatin in varied concentrations.

These concentrations were utilized for bevacizumab: 1.5-500 nM. The media was aspirated out and 200 μl of fresh serum free media was added to each well at the end of 24 hours. The MTT reagent (Sigma Aldrich, MO), i.e., 3-(4,5-dimethylthiazol-2-yl)-2,5-diphenyl tetrasodium bromide), (20 μl of 5 mg/ml MTT dissolved in PBS pH 7.4) was added to each well and incubated at 37° C. for 3 h. The medium was aspirated out and the formazan crystals formed were dissolved in 200 μl of DMSO. After adding DMSO, the crystals dissolved and the color absorbance was measured at 570 nm using a microplate reader. In the next experiment, tumstatin or transferrin-tumstatin was used instead of bevacizumab in the following concentrations: 7.8-1000 nM. The same methods, as described above, were followed. Transferrin-tumstatin protein was used in the concentrations of 1.5-500 nM (n=3 for each concentration).

Tube Formation Assay:

Matrigel® was thawed at 4° C. overnight. A 48 well plate was prepared for the tube formation assay by spreading 75 μl of the thawed matrigel in the bottom of each of the wells. The plate was kept at 37° C. for 30 minutes to polymerize the matrigel. Choroidal endothelial cells were transferred to the 48 well plate containing the matrigel. Each well contained $6 \times 10^3$ cells. Three wells were kept as control with no tumstatin incorporated. The additional 45 wells contained the tumstatin protein in the concentrations described above for the proliferation assay. The plate was kept at 37° C. for 18 hours. Tube formation was analyzed using a light microscope. The same methods were used to conduct the transferrin-tumstatin and bevacizumab protein experiments. Concentrations ranging from 0.15 to 500 nM (n=3 for each concentration) were utilized.

Cell Migration Assay:

In vitro cell migration assays were performed using a Matrigel invasion chamber (8-μm pore size, Becton Dickinson, Mass.). A suspension of $5 \times 10^5$ cells in 0.5 ml of serum free media were added to the Matrigel chamber. Wells were filled with 1 ml of 10 ng/ml VEGF solution. The chambers were incubated at 37° C. for 24 hours in a 95% air/5% $CO_2$ incubator. The cells on the lower surface of the membrane were stained with Haematoxylin and Eosin stain. The invading cells were photographed under a Nikon microscope at 40× magnification and counted in five fields of three membranes for each concentration. The same methods were used to conduct the transferrin-tumstatin and bevacizumab protein experiments. Concentrations ranging from 0.15 to 500 nM (n=3 for each concentration) were utilized.

Molecular Docking:

An Accelery's discovery visualizer v2.5.1.9167 (Accelry's, Inc. CA) was used to study in silico docking of tumstatin and transferrin-tumstatin to the αVβ3 integrin receptor. The crystal structure of the non-collagenous domain of collagen IV (PDB #1LI1) was used as a reference to develop a homologous model for tumstatin. The crystal structure of iron-free human serum transferrin (PDB #2HAV) was used as a reference to develop a homologous model for transferrin. The proteins were prepared and energy minimization performed. Transferrin-tumstatin fusion proteins were created by fusing tumstatin to the C terminus of transferrin with a peptide bond. For the tumstatin with αVβ3 integrin docking studies, a homology model of tumstatin was used as a ligand and docked onto the crystal structure of the extracellular domain of αVβ3 integrin (PDB #1JV2). For the transferrin-tumstatin with αVβ3 integrin docking studies, the fusion protein was docked to the αVβ3 integrin receptor (PDB #1JV2).

Apoptosis Assay:

Apoptosis was studied using the DeadEnd colorimetric TUNEL (TdT-mediated dUTP nick end labeling) system (Promega Corporation, WI). Choroid endothelial cells ($1 \times 10^5$ cells/well) were plated on cover slips in a 12 well plate and allowed to adhere for 24 hours. After 24 hours, the cells were exposed to different concentrations of bevacizumab (1, 10 and 100 nM), tumstatin (100, 250 and 500 nM), and transferrin-tumstatin (1, 10 and 100 nM) protein. After 24 hours of protein exposure the cells were then washed, fixed with 4% paraformaldehyde, and permeabilized using 0.2% Triton® X-100 solution in phosphate buffer pH 7.4. The cells were further stained as per the standard protocol provided along with the DeadEnd™ colorimetric TUNEL assay system. The cells were studied under a light microscope at 40× magnification.

Induction of CNV in Brown Norway Rats and Choroidal Flatmounts:

Adult male brown norway rats (150-180 g) were purchased from Harlan Sprague Dawley Inc. (Indianapolis, Ind., USA). Rats were anesthetized using an intraperitoneal injection of 40-80 mg/ml ketamine and 10-12 mg/kg xylazine mixture. Induction of laser burns was performed as follows. Pupils were dilated by topical administration of 1% tropicamide solution. The fundus was visualized after placing a coverslip on the eye and insillation of 2.5% hypromellose solution. Eight laser spots (100 mm, 150 mW, 100 ms) concentric with the optic nerve were placed in the right eye of each rat using a 532 nm diode laser (Oculight Glx; Iridex Inc., Mountain View, Calif., USA) and a slit lamp (Zeiss slit lamp 30SL; Carl Zeiss Meditec Inc., Dublin, Calif., USA). Left eye was used as a control for each animal. The Bruch's membrane breakage was confirmed by the end point "bubble formation". Rats showing intraocular hemorrhage on laser administration were excluded from the study. CNV lesions were allowed to develop for 14 days after induction of laser burns. At the end of 14 days, rats were administered one of the following treatments intravitreally, (a) PBS pH 7.4, (b) bevacizumab, (c) tumstatin protein, and (d) transferrin-tumstatin protein. Rats were euthanized at the end of 14 days of treatment and eyes enucleated.

For choroidal flatmount, the rats anesthetized using an intraperitoneal injection of 80 mg/kg ketamine and 10 mg/kg xylazine mixture. Rats were infused with 10 ml of PBS (pH 7.4) followed by infusion with 10 ml 4% paraformaldehyde. Finally, 4 ml of 50 mg/ml fluorescein isothiocyanate (FITC)-dextran solution ($2\times10^6$ Da) was infused. The eyes were then enucleated and flatmounts prepared. The flatmounts were imaged with a Nikon EZ-C1 confocal microscope using 488 and 568 nm excitation wavelengths. CNV areas were obtained using ImageJ software.

Results

Construction of Plasmids:

Picture of 1% agarose gel were taken (not shown) of tumstatin, tumstatin-EGFP, transferrin-tumstatin-EGFP, and transferrin-tumstatin plasmid, which were 5813, 6521, 8550 and 7842 base pairs, respectively. A 1Kb DNA ladder was run as a size marker. The SDS gel electrophoresis image of tumstatin (28 kDa) and transferrin-tumstatin-EGFP (135 kDa) protein were also taken (not shown). An electropherogram was also taken for base pair sequencing result for tumstatin after its insertion in PSecTag2B. Sequencing was done using capillary electrophoresis (Applied Biosystems, CA). Expression of tumstatin-EGFP gene was studied in ARPE cells and images were taken (not shown). Confocal microscopy pictures (100×) of ARPE cells expressing the tumstatin-EGFP protein were also taken (not shown). DAPI staining was performed to stain cell nuclei. ARPE cells with no tumstatin-EGFP transfection were used as controls to cancel out any background fluorescence.

Internalization of transferrin-tumstatin-EGFP protein was determined. Intense EGFP signal was observed in RF/6A cells upon exposure to transferrin-tumstatin-EGFP protein. Any protein on cell surface was expected to be removed by acidic buffer washes. This was due to the pKa of the lipid phospholipids that constituted the cell membrane. The lowest pKa of the phosphate groups is ~2, which indicates that the phosphate groups will either be in an uncharged state of $H_3PO_4$ or have a single negative charge ($H_2PO_4^-$) at pH 2. At pH higher than ~2, the probability of having two negative charges ($HPO_4^{-2}$) increases. Therefore the EGFP signal was supposed to be due to the internalized protein only. Exposure of RF/6A cells to the tumstatin-EGFP protein resulted in no observable internalization.

Polarized Secretion of Transferrin-Tumstatin-EGFP Fusion Protein:

MDCK cells were used to study the basolateral secretion of the transferrin-tumstatin-EGFP protein. The images taken of this experiment showed that the transferrin-tumstatin-EGFP protein was secreted on the basolateral side of the cells. When the basolateral side was examined under a confocal microscope, the cell boundaries were not visible. This may be the result of the porous nature of the transwell filters that does not allow light to be reflected back to the microscope and can also hinder light path to the cells. This can be a possible reason for lack of visibility of cells from the filter's basolateral side. Although cells were not visible from the basolateral side, DAPI staining and EGFP signal from the secreted protein can clearly be observed on the basolateral side. Cells can clearly be observed when filter's apical side was studied under a confocal microscope. Protein secretion was observed on the basolateral surface of the cells. Such occurrence can be explained in at least two ways. The protein may be bound to the receptors on the cell surface, or the protein may be embedded in the filter (for the basolaterally secreted protein). A quantification of the protein secreted in the basolateral and apical medium further confirmed the secretory pathway of the transferrin-tumstatin-EGFP protein.

Transferrin-tumstatin-EGFP protein collected from the apical and basolateral media was purified. The protein content in the apical and basolateral media was determined. The apical media contained 23.17% and the basolateral side contained 76.83% of the transferrin-tumstatin-EGFP protein. The total protein secreted in both media was considered to be 100%. Tumstatin-EGFP protein (control) was purified from the apical and basolateral media collected after the completion of polarized MDCK cell study. The apical media contained 68.84% and the basolateral side contained 31.16% of the tumstatin-EGFP protein. These data show that having a transferrin-tumstatin fusion protein can significantly increase the basolateral secretion of the fusion protein. In the absence of transferrin, tumstatin was secreted more on the apical side (68.84%) in comparison to only 23.17% being secreted apically in the presence of transferrin in the fusion protein.

Figure 1:
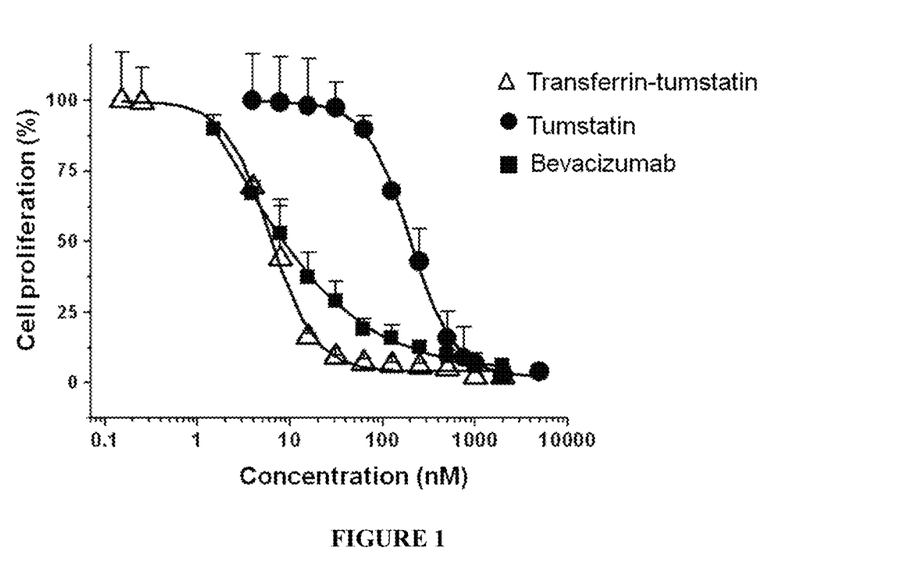
FIG. 1 is a graph showing anti-proliferative activity of transferrin-tumstatin, bevacizumab, and tumstatin.

Cell Proliferation Assay:

Cell proliferation induced by VEGF 165 was inhibited by the presence of tumstatin and transferrin-tumstatin protein. FIG. 1 shows the cell proliferation under the effect of tumstatin, transferrin-tumstatin and bevacizumab proteins. MTT assay was used to judge the anti-proliferative activity of tumstatin (●), transferrin-tumstatin (Δ) and bevacizumab (■) on choroidal endothelial cell proliferation stimulated by VEGF (50 ng/ml). Absorbance after treatment with MTT reagent was measured using UV-Vis spectrophotometer. Data is expressed as mean±S.D. for n=3. As the graph shows, transferrin-tumstatin protein was highly efficacious in reducing cell proliferation when compared to tumstatin alone. The $IC_{50}$ of the transferrin-tumstatin protein was found to be 5.97 nM. It was found to be 185.7 nM for the tumstatin protein alone. Bevacizumab was also tested for inhibition of cell proliferation and its efficacy was found to be at an $IC_{50}$ of 7.78 nM.

Transferrin-tumstatin protein was more efficient at inhibiting cell proliferation than Bevacizumab. Transferrin-tumstatin was also able to inhibit a greater number of cells, above the $IC_{50}$ of the protein, in comparison to bevacizumab. At a concentration of 15.6 nM transferrin-tumstatin inhibition was nearly 84% whereas bevacizumab inhibition is ~63%.

Figure 2:
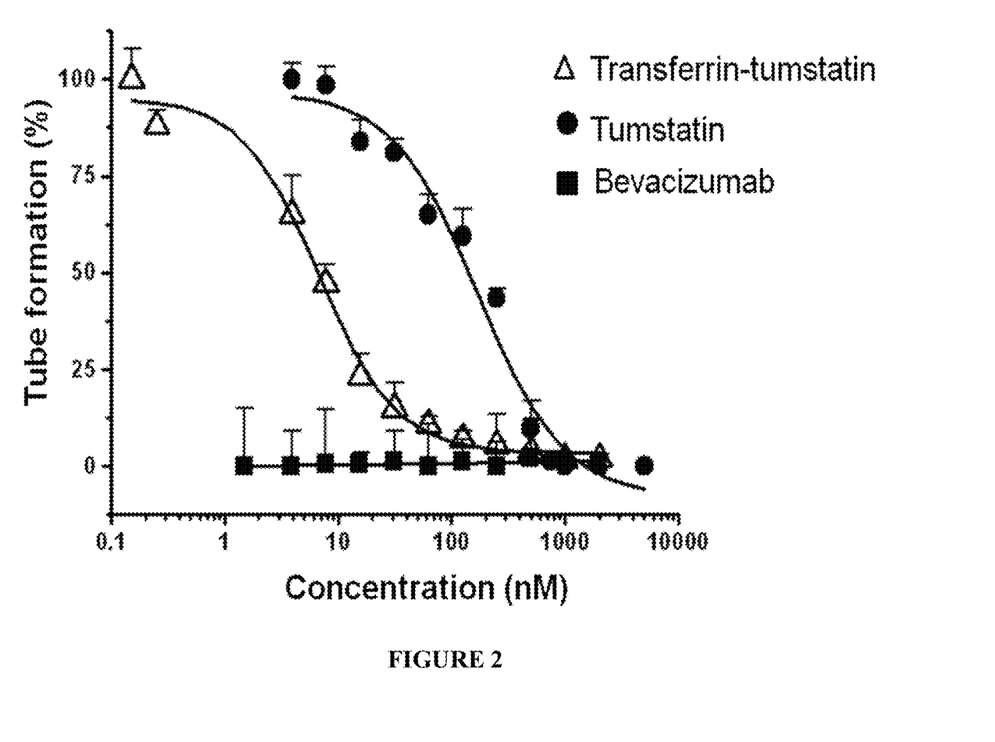
FIG. 2 is a graph showing inhibition of endothelial tube formation observed in choroid endothelial cells with different concentrations of tumstatin, transferrin-tumstatin and bevacizumab protein.

Tube Formation Assay:

Representative images (not shown) of tube formation were taken under different concentrations of tumstatin, transferrin-tumstatin and bevacizumab. Tube formation was seen to decrease with increase in concentration of tumstatin and transferrin-tumstatin protein. Both tumstatin and transferrin-tumstatin protein were able to inhibit tube formation, whereas no noticeable inhibition of tube formation was observed under the effect of bevacizumab. In the tube formation assay performed using transferrin-tumstatin fusion protein, a substantially complete prevention of formation of tubes was observed at 125 nM concentration. FIG. 2 shows a sigmoidal fit graph of all the three proteins tested. Tube formation was evaluated after 18 hours. Data is expressed as mean±S.D. for n=3.

Invasion Assay:

Invasion assay mimics the basement membrane in vivo and cells tend to migrate towards a chemoattractant such as VEGF. Images showed the decrease in number of invading cells under the effect of tumstatin and transferrin-tumstatin protein. Significant decrease in the number of cells invading the Matrigel invasion chamber membrane was observed as the concentration of tumstatin protein was increased in the media. Images (not shown) of cells invading membrane under the effect of tumstatin and transferrin-tumstatin were also taken. VEGF (10 ng/ml) was used as the chemoattractant and it showed considerable invasion of the membrane in the absence of either tumstatin or transferrin-tumstatin protein. However, the effect of VEGF in inducing membrane invasion was reduced in the presence of either of the two proteins, even though VEGF was present. This indicates to the efficacy of tumstatin and transferrin-tumstatin protein in reducing cell migration and invasion even in the presence of stimulants such as VEGF.

The invasion was reduced significantly by transferrin-tumstatin protein when compared to only tumstatin protein. The effect of transferrin-tumstatin protein was significantly different than tumstatin at the concentrations of 15 and 125 nM (P<0.05). However, the difference was not substantially significantly at higher concentrations of 250 and 500 nM. This indicates that the invasive tendency was saturated (the cells are no more invasive and attracted towards VEGF) and further invasion was not affected at higher concentrations. This effect is different than that observed in cell proliferation and tube formation studied using the two proteins. Bevacizumab exhibited lower $IC_{50}$ values of 8.0 nM in comparison to 12.14 nM for transferrin-tumstatin and indicates an important role of VEGF in cell invasion.

Molecular Docking:

Molecular models were made in silico for tumstatin and transferrin-tumstatin docked to the αVβ3 integrin receptor. The energy values for the two different docked proteins indicated that the docking of transferrin-tumstatin (interaction energy of −130.43 kcal/mol) is more energetically favorable than the docking of tumstatin (interaction energy of −113.28 kcal/mol) alone.

Apoptosis Assay:

Representative images (not shown) were taken of cells exhibiting apoptosis under the effect of tumstatin, transferrin-tumstatin and bevacizumab. Tumstatin and transferrin-tumstatin protein induced apoptosis in choroid endothelial cells at all three concentrations tested (100, 250 and 500 nM and 1, 10 and 100 nM, respectively). No significant apoptosis was induced by bevacizumab (1, 10 and 100 nM concentrations) and was similar to what was observed in control PBS.

Figure 3:
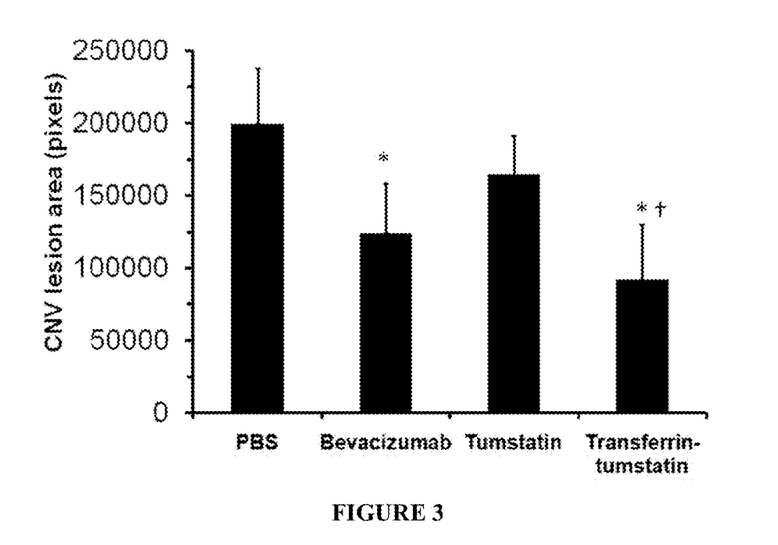
FIG. 3 is a bar graph showing in vivo assessment of CNV lesion size in BN rats.

Induction of CNV in Brown Norway Rats and Choroidal Flatmounts:

Transferrin-tumstatin was found to be more efficacious in reducing laser induced CNV lesion area as compared to bevacizumab and tumstatin (FIG. 3). CNV lesion size was quantified at the end of 14 days of treatment in choroidal flatmounts. A quantitative comparison of the CNV lesion size is shown in FIG. 3 (* indicates p<0.05 when compared to tumstatin treatment. † indicates p<0.05 when compared to bevacizumab. Data is expressed as mean±S.D. for n=42-48 lesions in each group). Transferrin-tumstatin treated rats had a significantly lower lesion size in comparison to bevacizumab and tumstatin treated rats.

Discussion

Some aspects of the invention provide a recombinant protein comprising transferrin that is linked to tumstatin. The recombinant proteins (in particular transferrin-tumstatin recombinant (e.g., fusion) protein) of the invention have enhanced binding to αVβ3 integrin and inhibited endothelial cell proliferation, migration, and tube formation with 21, 25 and 31-fold higher activity, respectively, relative to tumstatin alone. Further, transferrin-tumstatin was shown to be more effective at inhibiting choroidal endothelial cell proliferation and tube formation compared to bevacizumab. Moreover, transferrin-tumstatin recombinant protein showed a superior efficacy for inhibiting CNV in vivo compared to transferrin alone. Other aspects of the invention provide a plasmid expression system that is capable of producing a recombinant protein comprising transferrin that is linked to tumstatin (i.e., transferrin-tumstatin fusion protein). In some embodiments, the plasmid expression system of the invention allows preferential secretion of the protein towards the basolateral side of confluent cell monolayers.

Experiments showed that recombinant protein of transferrin-tumstatin inhibited endothelial cell proliferation ($IC_{50}$ of 5.97 nM) with 31-fold and 1.3-fold greater potency than tumstatin ($IC_{50}$ of 185.7 nM) and bevacizumab ($IC_{50}$ of 7.78 nM), respectively. Without being bound by any theory, it is believed that the 31-fold greater efficacy of transferrin-tumstatin over tumstatin and 1.3-fold better activity over bevacizumab is the result of two possible mechanisms. First, it is believed that transferrin improved the binding efficiency of tumstatin to αVβ3 integrin receptor. Using in silico modeling, the present inventors have determined that transferrin has binding interactions with αVβ3 integrin. In silico modeling also showed that the fusion protein exhibited better interaction energy than tumstatin alone (−130.43 kcal/mol vs −113.28 kcal/mol). The second possible mechanism of improved activity of recombinant protein transferrin-tumstatin is believed to be internalization of the fusion protein. It was observed that transferrin-tumstatin is internalized by choroidal endothelial cells. This internalization was not evident for tumstatin.

It is possible that transferrin-tumstatin may also be acting via a pathway that is activated only after internalization. Other endogenous antiangiogenic proteins such as endostatin and angiostatin have been shown to form complexes with RGD containing proteins such as fibronectin and vitronectin. Complex formation is essential for activity of these antiangiogenic proteins and these proteins were found to be inactive in mice lacking either fibronectin or vitronectin. Fibronectin is secreted by endothelial cells in a significant amount (~3.0 μg/$10^5$ cells/day), and once internalized, accumulation of RGD containing proteins such as fibronectin in the cytoplasm of the cell induces apoptosis. Thus, it is possible that fusion of transferrin to tumstatin increases the cytoplasmic content of RGD containing proteins such as fibronectin, thereby causing apoptosis of cells. This possibility is not significant for tumstatin as it did not show any signs of internalization in experiments. For tumstatin, its binding to αVβ3 integrin is believed to be the principal mechanism of action.

Again without being bound by any theory, it is believed that recombinant protein of transferrin-tumstatin inhibits cell proliferation by inhibiting protein synthesis and inducing apoptosis, similar to tumstatin alone. The present inventors have observed greater anti-apoptotic activity for recombinant transferrin-tumstatin protein than tumstatin alone. Bevacizumab did not exert any observable apoptotic activity in choroid endothelial cells. Lack of apoptotic activity has been previously reported for bevacizumab in corneal endothelial cells, retinal ganglion cells, and retina-RPE-choroid cultures.

Experiments showed that recombinant protein of transferrin-tumstatin inhibited tube formation in choroidal endothelial cells with 25 fold more efficacy than tumstatin alone. It is believed that internalization of recombinant protein of transferrin-tumstatin leads to complex of transferrin-tumstatin and fibronectin that can bind to other activated endothelial cells more strongly and prevent tube formation. Bevacizumab did not show any noticeable inhibition of tube formation in choroidal endothelial cells. It is generally believed that tube formation occurs under the effect of collagen IV, VIII, XV, XVIII, and laminin 8 and 10, which are present in the basement membrane. These components tend to promote stability, adhesion, and migration of endothelial cells. Growth factors such as VEGF are also present in the basement membrane matrix. However, VEGF does not appear to play an important role in tube formation, as tube formation occurs with high efficiency even in the presence of bevacizumab, which is known to act by neutralizing VEGF in the extracellular matrix.

It is believed that during angiogenesis, after degradation of basement membrane, endothelial cells migrate onto a provisional basement membrane-like matrix. VEGF is known to play an important role in the migration of endothelial cells, and the present inventors have studied this process using a Boyden chamber cell migration assay. One of the purposes of this assay was to assess the impact of VEGF on invasion of basement membrane by endothelial cells that are further going to form blood vessels. Cell migration under the effect of 10 ng/ml of VEGF was significantly lower when recombinant protein transferrin-tumstatin was used than when tumstatin was used alone. It has been shown that tumstatin inhibits focal adhesion kinase (FAK) phosphorylation. Lack of FAK activation eventually leads to inhibition of cell migration. It is believed that recombinant protein transferrin-tumstatin exerts similar effects, although to a greater extent.

Another major advantage of fusing transferrin to tumstatin is the preferential basolateral secretion of the fusion protein. Nearly 75% of recombinant protein transferrin-tumstatin was secreted towards the basolateral side of the cell in comparison to only ~35% of tumstatin protein alone. This provides recombinant protein transferrin-tumstatin with the capability to target the proliferating choroid endothelial cells following intravitreal drug delivery. After intravitreal delivery of therapeutic agents, RPE cells act as a barrier to further movement of therapeutic agents due to the tight junction nature of these cells. Transferrin-tumstatin is advantageous over tumstatin or bevacizumab by virtue of its basolaterally secreting nature. Intravitreally administered transferrin-tumstatin places tumstatin towards the choroid endothelial cells and in close vicinity to the site of disease.

In vivo studies indicated the superior efficacy of transferrin-tumstatin in inhibiting choroidal neovascularization. Lesion size in BN rats eyes treated with transferrin-tumstatin was significantly lower compared to rats treated with bevacizumab or tumstatin.

These results indicate that transferrin-tumstatin is a better therapeutic agent than bevacizumab because among other things (a) transferrin-tumstatin is a better inhibitor of cell proliferation than bevacizumab, (b) transferrin-tumstatin induces cell apoptosis in choroid endothelial cells, which is absent with bevacizumab, (c) transferrin-tumstatin inhibits tube formation, whereas bevacizumab is ineffective in inhibiting tube formation. In comparison to tumstatin alone, transferrin-tumstatin exerts ≥20-fold potency in all the in vitro assays used to assess neovascularization. More significantly, transferrin-tumstatin was more efficacious in vivo in reducing laser induced CNV compared to bevacizumab and tumstatin.

Example 2

Production and Purification Tf-T Protein

The PSecTag2B vector used to construct plasmids has a six histidine tag that helps in purification of the protein secreted in the media. ARPE cells (passage #24) were grown in a 12 well plate till 80% confluency. Amplified Tf-T (transferrin-tumstatin) plasmid (cloned in PSecTag2B vector) was diluted in DMEM/F12 media and mixed with lipofectamine reagent. The plasmid and lipofectamine complex was added to each well containing cells and media. The complex was mixed gently by rocking the wells back and forth. The cells were incubated at 37° C. in a 5% $CO_2$ incubator for 24 hours. At the end of 24 hours, media was collected and purified. TALON® metal affinity resin was used to purify the fusion protein. The media collected from the cells was mixed with the resin and incubated for 20 minutes at room temperature with mild agitation. Protein bound to the resin was eluted using an aqueous solution of 50 mM sodium phosphate, 300 mM sodium chloride, and 150 mM imidazole at pH 7.0. Later, imidazole was removed from the protein solution by dialyzing (using a 2000 MWCO dialysis bag) against a similar buffer without imidazole. BCA® Protein Assay Kit was used to estimate the protein content. Three separate batches were purified as described and assessed for reproducibility using SDS gel electrophoresis (PAGE), fluorescence spectroscopy, and circular dichroism.

For gel electrophoresis, 5 µg of protein was mixed with 4× loading dye and boiled for 5 minutes. Samples were run on 4-20% gradient SDS-PAGE gel (Bio-Rad, Hercules, Calif.). Circular dichroism (CD) in the far-UV spectral region (190-250 nm) was used to study Tf-T and tumstatin secondary structure. CD spectra were obtained on an AVIV model 62 DS spectropolarimeter (AVIV Biomedical, Inc., NJ). Protein solution was transferred into a 1 mm path length quartz cell and placed in a thermostatic cell holder. Data were collected at 0.25 nm intervals utilizing a 2 nm bandwidth. A 100 nM solution of tumstatin and Tf-T was prepared in 5 mM phosphate buffer pH 7.4. Fluorescence spectroscopy was performed by exciting the protein at 280 nm. Emission spectrum was collected from 300-400 nm wavelengths. The experiment was performed in a Spectramax M5 microplate reader (Molecular Devices, LLC).

Characterization of Tumstatin and Tf-T Protein:

Characterization of Tf-T was performed using SDS gel electrophoresis (PAGE), size exclusion chromatography (SEC), circular dichroism, and dynamic light scattering. For gel electrophoresis, 5 µg of protein was mixed with 4× loading dye and boiled for 5 minutes. Samples were run on 4-20% gradient SDS-PAGE gel (Bio-Rad, Hercules, Calif.). SEC was performed using an Agilent SEC-3 column (I.D. 7.8 mm and length 300 mm). The flow rate for the injected samples was 1 ml/minute. The sample volume injected was 25 µl. Mobile phase used for SEC was phosphate buffer saline (PBS) pH 7.4.

CD in the far-UV spectral region was used to study Tf-T and tumstatin secondary structure. CD spectra were obtained on an AVIV model 62 DS spectropolarimeter (AVIV Biomedical, Inc., NJ). Protein solution was transferred into a 1 mm pathlength quartz cell and placed in a thermostatic cell holder. Data were collected at 0.25 nm intervals utilizing a 2 nm bandwidth. Malvern Nanosizer was used to evaluate the particle size of a 1 mg/ml solution of tumstatin and Tf-T.

Secretion of Tumstatin and Tf-T Fusion Protein:

For protein secretion study, RPE cell monolayer was chosen to evaluate the secretion pattern of Tf-T. Initially cells were characterized for their electrical resistance, tight junction formation, and nuclear staining pattern. RPE cells were plated on Transwell filters and transepithelial electrical resistance (TEER) was measured using an EVOM® resistance meter (World Precision Instruments, CA). When TEER was >200 Ω·cm², tight junction formation was also confirmed by ZO-1 staining Filters with cells having a TEER>200 Ω·cm² were fixed for 30 minutes at room temperature by addition of 10% formalin (0.5 ml on apical and 1.5 ml on basolateral side). Cells were further permeabilized by adding 0.1% triton X 100 containing 5% goat serum (0.5 ml on apical side) for 1 hour at room temperature. Primary ZO1 antibody (0.5 ml on apical side), diluted to 1:100 dilutions, was added to the cells and incubated for 1 hour at room temperature. Secondary FITC labeled antibody (0.5 ml on apical side), diluted to 1:100 dilutions, was added to cells and incubated for 1 hour at room temperature. Cells were incubated with 3 µg/ml DAPI (4',6-diamidino-2-phenylindole) for 5 minutes to stain the nuclei. Filters were cut out with a sharp blade and transferred to a glass slide, fixed by adding SuperMount mounting media (BioGenex, CA) and visualized under a confocal microscope.

To evaluate the secretion pattern, cells were incubated with 200 µg tumstatin or Tf-T protein on the apical side. After 24 hours of transfection, the media was collected from both the basolateral and the apical side separately and purified using TALON metal affinity resin. Tumstatin and Tf-T proteins were quantified using a BCA® protein assay kit.

Stability of Tf-T Protein:

Tf-T protein was assessed for its stability in (a) pH 4.0 and 8.0 buffers, (b) tris(hydroxymethyl)aminomethane (TRIS) and phosphate citrate buffer at pH 7.0, and (c) ionic strengths ranging from 10 mM to 250 mM sodium chloride at pH 7.0. The protein solutions were exposed to the mentioned conditions for 48 hours and stability assessed using circular dichroism and fluorescence spectroscopy. SDS PAGE was used in addition of circular dichroism and fluorescence spectroscopy to assess pH stability.

Early time point efficacy studies in CNV induced Brown Norway rats: Adult male Brown Norway (BN) rats (150-180 gm) were purchased from Harlan Sprague Dawley Inc. (Indianapolis, Ind., USA). Rats were anesthetized using an intraperitoneal injection of 40-80 mg/ml ketamine and 10-12 mg/kg xylazine mixture. Induction of laser burns was performed as described in Example 1. CNV lesions were allowed to develop for 7 days after induction of laser burns. At the end of 7 days, rats were administered one of the following treatments intravitreally, (a) PBS pH 7.4, (b) bevacizumab, or (c) Tf-T protein. The development of CNV lesions before and after treatment was monitored using fluorescein angiography. For fluorescein angiography, rats were anaesthetized, pupils were dilated by topical administration of 1% tropicamide solution, and 200 µl of a 1% sodium fluorescein was administered to rats through the tail vein. Leakage from the lesions was immediately monitored using Genesis Df fundus camera (Kowa Optimed Inc, CA). CNV areas were obtained using ImageJ software.

Results

Production and Purification of Tf-T Protein:

Single bands of 100 Kda Tf-T protein were attained in the three batches of Tf-T prepared and tested. Tf-T produced by the described method had similar fluorescence and circular dichroism spectra.

Characterization of Tumstatin and Tf-T Protein:

A single band at 100 kDa and 28 kDa in SDS PAGE and a single peak in SEC showed the purity of Tf-T and tumstatin. Particle size for Tf-T was 8.0 nm with a polydispersity index (PDI) of 0.414. Particle size of tumstatin was 3.9 nm with a PDI of 0.359. CD scan of Tf-T circular dichroism spectra indicated that Tf-T has a majority of β sheets and turns (~60%) along with the presence of α-helices too (~32%). Tumstatin's structure is also rich in β sheets and turns (~50%). However, tumstatin has less α-helices (~16%) and has more of a random coiled structure (~40%). Therefore, the circular dichroism spectra are different for both the proteins.

Secretion of Tf-T Fusion Protein:

RPE cells formed tight junctions when grown on a Transwell filter for 4 weeks. Tight junction formation was also confirmed by the staining of ZO-1 protein. The RPE cells showed a clear staining pattern for ZO-1 and outlined the uniform polygonal shape of the RPE cells within the monolayer. Following apical exposure of the proteins, RPE cells secreted 126.8 µg/ml of Tf-T protein to the basolateral side. On the contrary, only 12.3 µg/ml tumstatin was secreted towards the basolateral side.

Stability of Tf-T Protein:

Tf-T was found to be most stable at pH 7.0. SDS PAGE showed that the band intensity decreases at pH 4-6 in comparison to the control Tf-T, indicating degradation of the protein. Furthermore, fluorescence and circular dichroism indicated a decrease in signal at all pH values except pH 7.0. As the protein was found to be most stable at pH 7.0, further stability studies (ionic strength and buffer) were performed at pH 7.0.

The fluorescence and circular dichroism spectra of Tf-T exposed to NaCl 10 mM to 250 mM in phosphate citrate and TRIS buffer were obtained. Tf-T showed no effect of ionic strength changes in the presence of phosphate citrate buffer. However, Tf-T signal was reduced in the presence of NaCl 250 mM and TRIS buffer. Thus, phosphate citrate buffer is better suited for the protein.

Early Time Point Efficacy Studies in CNV Induced Brown Norway Rats:

When treatment was initiated at an earlier time point (7 days after CNV induction) Tf-T treated rats had a lower lesion size compared to bevacizumab treated rats. This indicates that Tf-T is efficacious as a preventive treatment for choroidal neovascularization.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A recombinant protein comprising full-length transferrin that is linked to the amino-terminus of tumstatin.

2. The recombinant protein of claim 1, wherein transferrin and tumstatin are directly linked to one another.

3. The recombinant protein of claim 1, wherein transferrin and tumstatin are covalently linked to one another through a linker.

4. The recombinant protein of claim 1, wherein tumstatin comprises a full-length tumstatin peptide.

5. A recombinant protein comprising transferrin that is linked to the amino-terminus of full-length tumstatin.

6. The recombinant protein of claim 5, wherein transferrin comprises full-length transferrin peptide.

7. A plasmid comprising a nucleic acid sequence encoding the recombinant protein of claim 1.

8. The plasmid of claim 7, wherein the nucleic acid sequence encoding the recombinant protein is operatively linked to an expression control sequence.

9. A recombinant nucleic acid molecule comprising a nucleic acid sequence encoding the recombinant protein of claim 1.

10. The recombinant nucleic acid molecule of claim 9, wherein the nucleic acid sequence is operatively linked to an expression control sequence.

11. A transfected cell that comprises a recombinant nucleic acid sequence encoding the recombinant protein of claim 1.

12. A method for producing a recombinant protein comprising transferrin that is linked to the amino-terminus of tumstatin, said method comprising: culturing the transfected cell of claim 11 under conditions sufficient to produce the recombinant protein comprising transferrin that is linked to tumstatin; and recovering the recombinant protein as a substantially purified recombinant protein.

13. The method of claim 12, wherein the recombinant protein comprises transferrin that is directly linked to tumstatin.

14. A method for treating a clinical condition associated with neovascularization or vascular leakage or hyperpermeability in a subject, said method comprising administering to the subject in need of such a treatment a therapeutically effective amount of the recombinant protein of claim 1, the plasmid according to claim 7, or the recombinant nucleic acid according to claim 9,
wherein said clinical condition is selected from the group consisting of diabetic retinopathy, neovascular glaucoma, corneal angiogenesis, wet age-related macular degeneration, and choroidal neovascularization (CNV).

* * * * *